United States Patent
Shroff et al.

(10) Patent No.: US 9,451,769 B2
(45) Date of Patent: Sep. 27, 2016

(54) FUNGICIDAL COMPOSITION COMPRISING MANCOZEB AND CHLOROTHALONIL

(71) Applicant: UPL Limited, Mumbai (IN)

(72) Inventors: Jaidev Rajnikant Shroff, Mumbai (IN); Vikram Rajnikant Shroff, Mumbai (IN); Philip Wayne Robinson, King of Prussia, PA (US); Beth Errickson Sears, King of Prussia, PA (US); Prakash Mahadev Jadhav, Mumbai (IN)

(73) Assignee: UPL Limited, Mumbai (IN)

( * ) Notice: Subject to any disclaimer, the term of this patent is extended or adjusted under 35 U.S.C. 154(b) by 0 days.

(21) Appl. No.: 14/436,882

(22) PCT Filed: Sep. 25, 2013

(86) PCT No.: PCT/IB2013/058833
§ 371 (c)(1),
(2) Date: Apr. 18, 2015

(87) PCT Pub. No.: WO2014/060880
PCT Pub. Date: Apr. 24, 2014

(65) Prior Publication Data
US 2015/0272125 A1    Oct. 1, 2015

(30) Foreign Application Priority Data
Oct. 18, 2012   (IN) .......................... 1194/KOL/2012

(51) Int. Cl.
*A01N 37/34* (2006.01)
*A01N 47/14* (2006.01)
*A01N 55/02* (2006.01)

(52) U.S. Cl.
CPC ............... *A01N 37/34* (2013.01); *A01N 47/14* (2013.01); *A01N 55/02* (2013.01)

(58) Field of Classification Search
None
See application file for complete search history.

(56) References Cited

PUBLICATIONS

Lorbeer et al., "Efficacy of Dicarboximide Fungicides and Fungicide Combinations for Control of Botrytis Leaf Blight of Onion in New York", Plant Disease, 1990, vol. 74, pp. 235-237.*

* cited by examiner

*Primary Examiner* — Savitha Rao
*Assistant Examiner* — Gregg Polansky
(74) *Attorney, Agent, or Firm* — Yancy IP Law, PLLC

(57) ABSTRACT

Disclosed herein is a fungicidal composition comprising combination of fungicidally effective amount of mancozeb and a fungicidally effective amount of chlorothalonil in a predetermined ratio.

16 Claims, No Drawings

FUNGICIDAL COMPOSITION COMPRISING MANCOZEB AND CHLOROTHALONIL

FIELD OF THE INVENTION

The present invention relates to a fungicidal combination comprising mancozeb and chlorothalonil. More particularly, the present invention relates to a fungicidal composition comprising the combination of mancozeb and chlorothalonil in a ratio of about 5:1.

BACKGROUND OF THE INVENTION

Mancozeb is a dithiocarbamate fungicide. It is the zinc ion coordination product with manganese ethylene-1,2-bisdithiocarbamate polymer, having the following chemical structure:

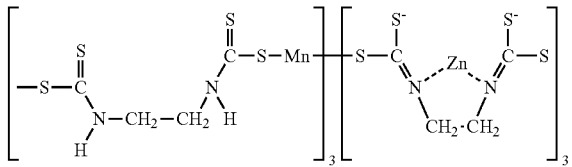

Mancozeb has a polymeric structure containing 1.6 percent zinc, in which 6 percent of the units are in the form of a coordination complex. Mancozeb is essentially inert to oxidation by atmospheric oxidation, in contrast with maneb. It is also essentially non-phytotoxic in contrast with maneb, zineb or mixtures of these which are harmful to a number of plants. The standard composition of mancozeb available in the art is an 80 percent wettable powder containing 16% manganese and 2% zinc. However, there are many disadvantages associated with the use of a powder composition. For example, U.S. Pat. No. 5,001,150 discloses removal of disadvantages associated with powder composition and teaches a non-dusty spray dried Mancozeb water dispersible granules (WDG) and the process for their production.

Chlorothalonil (2,4,5,6-tetrachloroisophthalonitrile) having chemical structure as below is a polychlorinated aromatic mainly used as a broad spectrum, nonsystemic fungicide, with other uses as a wood protectant, pesticide, acaricide, and to control mold, mildew, bacteria, algae. Chlorothalonil-containing products are sold under the names Bravo, Echo, and Daconil. It was first registered for use in the US in 1966. In 1997, the most recent year for which data are available, it was the third most used fungicide in the US, behind only sulfur and copper, with some 12 million lb used in agriculture alone that year. The EPA estimates, on average, almost 15 million lb were used annually from 1990-1996, including the non-agricultural uses.

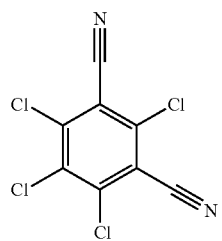 [SMILES: N#Cc1c(Cl)c(Cl)c(Cl)c(C#N)c1Cl]

The article titled "Fungicides to Control Early and Late Blight on Russet Norkotah Potatoes" Steven R. James and Frederick J. Crowe, discloses an experiment to evaluate the efficacy of selected fungicides on early and late blight control on Russet Norkotah potatoes. The article discloses Dithane+Bravo WS at the rate of 3.20 pt/a+1.50 pt/a (Dithane-mancozeb, Bravo-Chlorothalonil) and Dithane/Bravo 3.2 pt/a applied individually. It was observed that there were no significant differences (p<5%) among the fungicide treatments except for the week of August 30 when more early blight infected plants were observed in the Dithane/Bravo (mancozeb/chlorothalonil) when applied individually. Therefore, although the combination of mancozeb with chlorothalonil is known, the precise concentrations at which the combination shows proper synergistic effect in treating fungal infection is not known.

JP 56-046804 discloses antifouling agent composed of an insoluble salt of dithiocarbamic acid and tetrachlorophthalonitrile at 1/1 ratio, thus showing low toxicity and giving no adverse effects on, e.g., the storage stability of antifouling paint preparations, color and coating films. The disclosed antifouling agent is used by mixing or dispersing it in resins for general coating such as natural resin, oil mixture, synthetic resin or synthetic rubber, when necessary, together with pigments and plasticizers. The resulting preparation is applied to the materials contacting with water such as ship bottom, fish net and other underwater constructions to prevent them from fouling by aquatic lives such as sea weeds or barnacle.

The use of fungicide combinations is a widespread and documented practice in the agricultural community. Fungicidal combinations offer significant advantages over individual applications including improved and extended fungal control, reduced fungicide application rates and costs, shorter contact times for improved results, less stringent use restrictions, improved selectivity, improved spectrum of fungi controlled, reduced cost and reduced residue problems. However, identifying appropriate fungicide application rates and ratio of the combinations is essential to achieve efficacious weed control. Hitherto, there have been no studies to determine the most-efficacious and synergistic ratios of mancozeb and chlorothalonil, at which ratio these fungicides synergistically complement each other's fungicidal properties not seen at other ratios.

Even though the combination of Mancozeb and chlorothalonil is known in the art, the same is not known to be synergistically effective in combating the fungal diseases. Thus there exists a need in the art for a composition comprising Mancozeb and chlorothalonil at a ratio which shows superior and effective control on fungal infections.

Objects of the Invention

The various embodiments of the present invention may, but do not necessarily, achieve one or more of the following advantages and/or objects:

An object of the present invention is to provide fungicidal composition comprising a combination of mancozeb and chlorothalonil useful in combating fungal infections.

Another object of the present invention is to provide fungicidal composition comprising a combination of mancozeb and chlorothalonil in a synergistic ratio for an efficacious fungal control.

Yet another object of the present invention is to provide fungicidal composition that is useful for effectively controlling late blight, *Alternaria* leaf spot control and also enhances the vigor/yield of the plant.

Another object of the present invention is to provide fungicidal composition which is having good suspensibility and dispersibility.

These and the other advantages may be realized by reference to the remaining portions of the specification.

SUMMARY OF THE INVENTION

In accordance with the above objectives, the present invention provides a fungicidal composition comprising a fungicidally effective amount of mancozeb and a fungicidally effective amount of chlorothalonil useful in combating fungal infection and exhibit remarkable fungicidal activities for pathogenic fungi such as foliar late blight, *Alternaria* leaf spot. The composition also increases the vigor/yield of the plant.

In an embodiment, the composition of the present invention comprises mancozeb and chlorothalonil in a ratio of about 5:1.

In another embodiment, the composition of the present invention comprises mancozeb and chlorothalonil in a ratio of about 5:1, wherein the total weight of mancozeb and chlorothalonil together is about 75% by weight of the composition.

Thus, in an embodiment, the combination of the present invention comprises about 62.5% by weight of mancozeb and 12.5% by weight of chlorothalonil.

In yet another aspect the present invention provides a fungicidal composition comprising a fungicidally effective amount of mancozeb and a fungicidally effective amount of chlorothalonil along with at least one agrochemically suitable adjuvant, wherein the ratio of said amounts of mancozeb and chlorothalonil is about 5:1.

In another aspect the present invention provides a method of treating a locus, said method comprising treating the locus with the composition comprising the combination of Mancozeb and Chlorothalonil, wherein said mancozeb and chlorothalonil are present within the composition in a ratio of about 5:1.

Additional features and advantages of the proposed invention will be apparent from the detailed description that follows, which illustrates by way of example, the most preferred features of the proposed invention which are not to be construed as limiting the scope of the invention described herein.

DETAILED DESCRIPTION OF THE PREFERRED EMBODIMENT(S)

Therefore, the present invention provides a composition comprising fungicidally effective amount of mancozeb and fungicidally effective amount of chlorothalonil, wherein mancozeb and chlorothalonil are present in a ratio of about 5:1.

In an embodiment the fungicidal composition comprising Mancozeb and chlorothalonil in a synergistic weight ratio of about 5:1 wherein the total weight of mancozeb and chlorothalonil together is about 75% by weight of the composition.

The term "fungicidally effective amount" of mancozeb and chlorothalonil, as used herein, shall denote an amount of manoozeb and chlorothalonil that can be used to control harmful fungi when used together.

The term "fungicidally effective amount of manoozeb" includes mancozeb being preferably, but not limited to, present in a composition from about 55% to about 65% by weight of the composition. In an embodiment, the term "fungicidally effective amount of mancozeb" includes mancozeb being present in an amount of about 62.5% by weight of the composition.

The term "fungicidally effective amount of chlorothalonil" includes chlorothalonil being preferably, but not limited to present in a composition from about 10% to about 15% by weight of the composition. In an embodiment, the term "fungicidally effective amount of chlorothalonil" includes chlorothalonil being present in an amount of about 12.5% by weight of the composition.

The term "about" used to qualify the amounts of mancozeb and chlorothalonil shall be interpreted to mean "approximately" or "reasonably close to" and any statistically insignificant variations therefrom. In another aspect the present invention provides a fungicidal composition comprising a combination of mancozeb and chlorothalonil in a synergistic ratio of about 5:1.

Preferably however, the specific amounts of mancozeb and chlorothalonil present within the compositions of the present invention is not particularly limiting as long as the ratio of about 5:1 is maintained.

In an exemplary embodiment, which is not to be construed as limiting, mancozeb is present in an amount of about 62.5% by weight of the composition and chlorothalonil is present in an amount of about 12.5% by weight of the composition.

It has been surprisingly found that (a) the combination of mancozeb and chlorothalonil in a weight ratio of about 5:1 elicited faster fungicidal activity than either fungicide alone; (b) the combination of mancozeb and chlorothalonil in a weight ratio of 5:1 resulted in greater increase in the fungicidal activity than the additive effects of mancozeb and chlorothalonil alone or in comparison to the fungicidal activity of mancozeb and chlorothalonil combination at ratios other than 5:1; and (c) combining lipid metabolism disruptor mancozeb with chlorothalonil in a weight ratio of 5:1 led to a greater than additive fungicidal activity, which is an evidence of synergistic fungicidal potentiation.

The fungicidal composition comprising combination of manoozeb and chlorothalonil is useful in combating fungal infection and exhibits remarkable fungicidal activities for pathogenic fungi such as foliar late blight or *Alternaria* leaf spot. The said composition also increases the vigor/yield of the plant.

In an embodiment the present invention describes a method of treating a locus, said method comprising treating the locus with the composition comprising fungicidally effective amount of Mancozeb and fungicidally effective amount of Chlorothalonil present in the ratio of about 5:1.

In an embodiment, the fungicidal composition of the present invention comprises mancozeb in an amount of about 62.5% w/w by total weight of the composition and chlorothalonil in an amount of about 12.5% w/w by total weight of the composition.

It should be noted however that the weight ratio of 5:1 or the individual amounts of manoozeb and chlorothalonil being 62.5% and 12.5% respectively, are based on the purity of the compounds used, assuming 100% pure substances. A person skilled in the art would understand that perfectly pure compounds may not be used or available ordinarily. Therefore, practically higher amounts of mancozeb and chlorothalonil may be used, depending upon the purity of the available substances, as long as the preferred ratio of about 5:1, based on the 100% purity, is maintained. A composition comprising such higher amounts of mancozeb and chlorothalonil is also intended to be within the scope of the present invention.

The fungicidal combination of the present invention is preferably formulated as a solid composition including, but not limited to, dust, powder, granules, pellets, tablets, dry flowable, wettable powder or water dispersible granules.

In an embodiment, the composition of the present invention is a water dispersible granular composition, wherein the active ingredients are combined with various carriers. Therefore, in this aspect, the present invention provides a water dispersible granular composition comprising mancozeb in an amount of about 62.5% w/w by total weight of the composition; chlorothalonil in an amount of about 12.5% w/w by total weight of the composition; and remaining amounts of an agriculturally acceptable excipient or carrier. These carriers may be organic or inorganic material which may be combined with the active ingredients so as to facilitate better spreadability as well as enable better contact with the target fungi. These carriers must be agriculturally acceptable and environmentally friendly. Carriers may include such dispersing agents, antifoaming agents, pH modifiers, surfactants, and other fillers which may be added in into a stable composition. However, the present inventors found that the preparation of a granular composition comprising mancozeb and chlorothalonil in a predetermined weight ratio of 5:1 is not straightforward and is plagued by many problems. The water dispersible granular composition comprising chlorothalonil and mancozeb wherein the composition displays superior attrition resistance, disperses rapidly in water and has good suspensibility in water once it is dispersed was a long felt need in the art.

In an embodiment, the water dispersible granular composition of each or any aspect or embodiment described hereinabove comprises at least one adjuvant selected from at least one dispersing agent, at least one wetting agent, at least one antifoam, at least one pH modifier, at least one surfactant and combinations thereof. The composition content of these adjuvants is not particularly limiting and may be determined by a skilled technician in the art according to the conventional protocols.

In one embodiment, the composition may contain ionic and nonionic dispersing agents to enable disintegration of granules in water with ease, such as salts of polystyrene sulphonic acids, salts of polyvinylsulphonic acids, salts of naphthalenesulphonic acid/formaldehyde condensates, salts of condensates of naphthalenesulphonic acid, phenolsulphonic acid and formaldehyde, and salts of lignosulphonic acid, polyethylene oxide/polypropylene oxide block copolymers, polyethylene glycol ethers of linear alcohols, reaction products of fatty acids with ethylene oxide and/or propylene oxide, furthermore polyvinyl alcohol, polyvinylpyrrolidone, copolymers of polyvinyl alcohol and polyvinylpyrrolidone and copolymers of (meth)acrylic acid and (meth)acrylic esters, furthermore alkyl ethoxylates and alkylarylethoxylates. The preferred dispersing agents include sodium naphthalene sulfonate-formaldehyde condensate, alkyl naphthalene sulfonate or a combination thereof. The dispersing agent is present in an amount of 2-20% w/w.

In an embodiment, the compositions of the present invention comprise at least one wetting agent selected from soaps; salts of aliphatic monoesters of sulphuric acid including but not limited to sodium lauryl sulphate; sulfoakylamides and salts thereof including but not limited to N-methyl-N-oleoyl-taurate Na salt; akylarylsulfonates including but not limited to akylbenzenesulfonates; akylnaphthalenesulfonates and salts thereof and salts of ligninsulfonic acid. In an embodiment, the wetting agent includes a blend comprising an alkali metal salt of akylnaphthalenesulfonate or an alkali metal salt of ligninsulfonic acid or a combination thereof. The wetting agent is present in an amount of 0.2 to 7% w/w.

In a preferred embodiment, the composition of the present invention comprises a wetting component comprising a wetting blend selected from an alkali metal salt of akylnaphthalenesulfonate or an alkali metal salt of ligninsulfonic acid or a combination thereof.

In an embodiment, the compositions of the present invention comprise at least one antifoaming agent which are usually employed for this purpose in agrochemical compositions. In an embodiment, the preferred antifoaming agents are selected from silicone oil and magnesium stearate or a suitable combination thereof. The antifoaming agent is present in an amount of 0.01 to 2% w/w.

In an embodiment, the compositions of the present invention comprise at least one pH modifier selected from organic and inorganic components that are usually employed in agrochemical compositions to modify the pH. In a non-limiting embodiment, the pH modifier may be selected from potassium carbonate, potassium hydroxide, sodium hydroxide and sodium dihydrogen phosphate. However, the choice of a pH modifier is not particularly limiting. The pH modifier is present in an amount of 0.1-2.0% w/w.

In an embodiment, the compositions of the present invention comprise at least one further surfactant selected from salts of polystyrenesulphonic acids; salts of polyvinylsulphonic acids; salts of naphthalenesulphonic acid/formaldehyde condensates; salts of condensates of naphthalenesulphonic acid, phenolsulphonic acid and formaldehyde; salts of lignosulphonic acid; polyethylene oxide/polypropylene oxide block copolymers; polyethylene glycol ethers of linear alcohols; reaction products of fatty acids with ethylene oxide and/or propylene oxide; polyvinyl alcohol; polyvinylpyrrolidone; copolymers of polyvinyl alcohol and polyvinylpyrrolidone; copolymers of (meth)acrylic acid and (meth)acrylic esters; and alkyl ethoxylates and alkylarylethoxylates. The surfactant is present in an amount of 0.1 to 25% w/w.

In another aspect, the present invention provides a process for the preparation of a water dispersible granular composition comprising:
(a) blending a fungicidally effective amount of mancozeb with a fungicidally effective amount of chlorothalonil optionally with at least one adjuvant selected from at least one wetting agent, at least one dispersing agent, at least one antifoam, at least one stabilizing agent, at least one pH modifier, at least one surfactant or combinations thereof and water, to prepare slurry with total solid content of about 50-58%;
(b) homogenizing said slurry by wet milling and sieving to remove course particles having diameter greater than about 1000 microns;
(c) spray drying the slurry of step (b) through nozzle to obtain the granules of 100-500 micron;
(d) drying the granules of step (c) in a fluid bed dryer; and
(e) packing the dried granules.

In an embodiment, the spray-drying step of any slurry described hereinabove was carried out at a predetermined inlet and outlet temperatures of the dryer. In a preferred embodiment, the inlet temperature varied from about 220 to about 260° C., whereas the outlet temperature varied from about 95 to 115° C.

The term "wet milling" as used herein is intended to mean the grinding of materials with a sufficient quantity of a liquid to form a slurry. The process of wet milling and apparatus therefore are conventionally known in the art and do not form a critical feature of the present invention.

The process step of "spray drying" is conventionally known in the art. The conventional process for spray drying generally involves concentrating the input slurry, atomization of the slurry, droplet-hot gas contacting, evaporative drying of the droplets and separation of the spray dried granules. It was found that the spray-dried product according to the present invention possessed improved flow properties, better distribution of the active ingredients within the granules and required less dispersing agent(s) than the wet bead milled formulation.

The formulation described above is a fungicidally efficacious and stable formulation. Also, the granules obtained by the process have superior attrition resistance, disperses rapidly in water and have good suspensibility in water once it is dispersed.

The formulation also demonstrates reduced toxicity, reduced use rates, lesser damage to the environment, as well as reduction in dust hazard.

EXAMPLES

The following examples illustrate embodiments of the proposed invention that are presently best known. However, other embodiments can be practiced that are also within the scope of the present invention. All of the agrochemical formulations, according to the scope of the present invention and exemplified below had excellent storage stability properties.

Example 1

Preparation of Synergistic Combination of Mancozeb 62.5% and Chlorothalonil 12.5%

| Sr. NO | Ingredients | Qty |
|---|---|---|
| 1 | Mancozeb Technical (b)62.5@84.5% | 73.83 |
| 2 | Chlorothalonil technical (b)13@96% | 13.4 |
| 3 | Sodium lignosulfonate | 9.27 |
| 4 | Sodium Lauryl Sulfate | 3 |
| 5 | SAG 1572 (Anti-foam) | 0.5 |
| 6 | Total | 100 |

Process of Manufacturing:

The required amounts of Mancozeb and chlorothalonil were blended with sodium lignosulfonate, Sodium Lauryl Sulfate SAG 1572 and suspended in water to form slurry. The slurry was homogenized using colloid mils and sieved (1000 micron) to remove course particles. The slurry was then sprayed into the spray drier through nozzles to give droplets with an average size in range of 150-500 micrometer. In the spray-drier, a hot inert air stream (temperatures ranging between 220° C. and 260° C.) evaporated the water out of the droplets to give spherical granules with a size ranging from 100 to 450 micron. The outlet temperature of the spray dryer (and thereby the temperature of the granules) varied between 95 and 115° C. Dust formed during this drying process was removed in a separate stream. Subsequently, the granules were further dried in a fluid bed dryer to remove the remaining moisture.

Example 2

Preparation of Combination of Mancozeb 62.5% and Chlorothalonil 12.5%

| | Ingredients | Qty |
|---|---|---|
| 1 | Mancozeb Tech 85% | 73.5 |
| 2 | Chlorothalonil @ 98% | 12.7 |
| 3 | Alkyl naphthalene sulphonate | 2 |
| 4 | Alkyl naphthalene sulphonate formaldehyde condensate | 3.78 |
| 5 | Sodium lignosulfonate | 8 |
| 6 | SAG 1572 | 0.02 |
| 7 | TOTAL | 100 |

Process of Manufacturing:

The required quantities of Mancozeb and chlorothalonil were blended with Alkyl naphthalene sulphonate, Alkyl naphthalene sulphonate formaldehyde condensate, sodium lignolsulfonate and SAG 1572 and suspended in water to form slurry. The slurry was homogenized using colloid mill and sieved (1000 micron) to remove course particles. The granulation was performed in a two steps i.e. by the process of spray-drying followed by fluid bed (after-)drying.

Suspensibility of the Composition of Present Invention:

| | | Example 1 | | Example 2 | |
|---|---|---|---|---|---|
| Sr No | Properties | 0 Day | 14 D AHS | 0 Day | 14 D AHS |
| 1 | Mancozeb content (% w/w) | 63.11 | 62.86 | 63.37 | 63.25 |
| 2 | Mnz suspensibility (% w/w) | 82.18 | 79.11 | 78.38 | 67.93 |
| 3 | Chlorothalonil Content (% w/w) | 12.58 | 12.51 | 12.03 | 11.71 |
| 4 | Chlorothalonil Suspensibility (% w/w) | 102.33 | 102.07 | 99.45 | 98.66 |
| 5 | pH (1% aq. dispersion) | 6.61 | 6.78 | 6.6 | 6.9 |
| 6 | Wet Sieve (200 BSS) (% Retention) | Nil | Nil | 0.04 | 0.06 |
| 7 | Moisture Content (% w/w) | 1.11 | 1.09 | 1.12 | 1.07 |
| 8 | Persistent Foam in ml after 1 Minute | 12 | 10 | Nil | Nil |
| 9 | Wettability in sec | 8 | 6 | 5 | 5 |

Field Trial:

Field tests of the compositions according to the present invention were conducted at various controlled trial sites. The performance of the fungicidal composition according to the present invention (Mancozeb 62.5% and chlorothalonil 12.5%) was compared against the known compositions of Chlorothalonil 75%; Mancozeb 75% and Mancozeb 60% and chlorothalonil 12.5% which were evaluated against foliar late blight and *Alternaria* leaf spot in potato and also the vigor/yield of the plant was tested.

The potato crop was planted in three plots and harvested after 5 months. The formulations tested were prepared and evaluated for early and late blight control in potatoes. The reported results were mean of four replications of each evaluation designed in randomized complete blocks. The treated plot size was 12 feet by 30 feet. A single randomized control plot was included in each block. About 15 gallons per acre of the tested formulations were applied. The data collection was based upon standard collection procedures prevalent in USA.

Trial 1:
Late blight percentage severity

| Formulation | Percentage severity of late blight |
| --- | --- |
| Chlorothalonil 75% (1.5 lb/acre) | 20 |
| Mancozeb 62.5 + Chlorothalonil 12.5 (1.5 lb/acre) | 10 |
| Mancozeb 60% + Chlorothalonil 15.0 (1.5 lb/acre) | 17 |

Trial 2:
Potato Yield CWT/Acre

| | |
| --- | --- |
| Chlorothalonil 75% (1.5 lb/acre) | 34 |
| Mancozeb 62.5 + Chlorothalonil 12.5 (1.5 lb/acre) | 44 |

Trial 3:
Plant vigor rating.

| | |
| --- | --- |
| Chlorothalonil 54%, 6 lbs per gallon (1.5 pt/A) | 50 |
| Mancozeb 75% (2 lb/A) | 44 |
| Mancozeb 60% + Chlorothalonil 15.0 (2 lb/acre) | 42 |
| Mancozeb 62.5 + Chlorothalonil 12.5 (1.5 lb/acre) | 70 |
| Untreated check | 39 |

Potato Late Blight Trial

All treatments applied weekly for 8 total applications. All plots were inoculated with late blight on July 31. The protocol as described above was followed.

Trial 4:
Percentage foliar late blight 37 DAI (September 6)

| Formulation | Percentage foliar late blight |
| --- | --- |
| Untreated | 52 |
| Mancozeb 62.5 + Chlorothalonil 12.5 (1.5 lb/acre) | 4.6 |
| Mancozeb 62.5 + Chlorothalonil 12.5 (2.0 lb/acre) | 3.9 |
| Mancozeb 60% + Chlorothalonil 15.0 (1.5 lb/acre) | 6.8 |
| Mancozeb 60% + Chlorothalonil 15.0 (2.0 lb/acre) | 6.4 |

Trial 5:
Percentage foliar late blight 45 DAI (September 14)

| Formulation | Percentage foliar late blight |
| --- | --- |
| Untreated | 91.3 |
| Mancozeb 62.5 + Chlorothalonil 12.5 (2.0 lb/acre) | 13.3 |
| Mancozeb 60% + Chlorothalonil 15.0 (2.0 lb/acre) | 33.8 |

Area Under Disease Progress Curve (45 DAI, September 14)

| Formulation | AUDPC |
| --- | --- |
| Untreated | 39 |
| Mancozeb 62.5 + Chlorothalonil 12.5 (2.0 lb/acre) | 2.3 |
| Mancozeb 60% + Chlorothalonil 15.0 (2.0 lb/acre) | 5.4 |

Mancozeb 62.5+Chlorothalonil 12.5 at 1.5 and 2.0 lb/acre was statistically superior to both corresponding rates of Mancozeb 60%+Chlorothalonil 15.0.

Trial 6: Comparative Evaluation of Various Ratios of Mancozeb+Chlorothalonil WG for Bio-Efficacy Against Late Blight (*Phytopthora infestans*) and Early Blight (*Alternaria solani*) of Potato.

Treatment Details:

| Treatment No. | Product | Dose/Acre |
| --- | --- | --- |
| T1 | Mancozeb 50.0% + Chlorothalonil 25% WG (2:1 Ratio) | 0.907 kg |
| T2 | Mancozeb 56.3% + Chlorothalonil 18.7% WG (3:1 Ratio) | 0.907 kg |
| T3 | Mancozeb 60.0% + Chlorothalonil 15.0% WG (4:1 Ratio) | 0.907 kg |
| T4 | Mancozeb 62.5% + Chlorothalonil 12.5% WG (5:1 Ratio) | 0.907 kg |
| T5 | Mancozeb 64.3% + Chlorothalonil 10.7% WG (6:1 Ratio) | 0.907 kg |
| T6 | Mancozeb 65.6% + Chlorothalonil 9.4% WG (7:1 Ratio) | 0.907 kg |
| T7 | Mancozeb 75% WP | 0.907 kg |
| T8 | Chlorothalonil 75% WP | 0.680 kg |
| T9 | Untreated Control | — |

Method and Time of Application:

Forty four days after transplanting at first appearance of the disease symptoms in the field, first spray of all the Mancozeb+Chlorothalonil WG combinations @0.907 kg/acre was given. At the same time sprays of straight products viz., Mancozeb 75% WP @0.907 kg/acre and Chlorothalonil 75% WP @0.680 kg/acre were imposed as per the treatment. The sprayer used for application was ASPEE Bakpack Sprayer (13 liters capacity) installed with triple action single type of hallow cone nozzle. Subsequent sprays with the same fungicides were given at 10 days interval after the first spray. One treatment served as an untreated control (water spray). Spray fluid used was 500 liters/ha for each spray. Percent disease index (PDI) was calculated by using formula adopted by Horsfall and Heuberger, 1942 as follows The percent disease index (PDI) was calculated by using the following formula, $$PDI = \frac{\text{Sum of Numerical Rating}}{\text{Total number of leaves observed} \times \text{Maximum rating}} \times 100$$

The percent disease control (PDC) was calculated by the following formula, $$PDC = \frac{PDI \text{ in control} - PDI \text{ in treatment}}{PDI \text{ in control}} \times 100$$

Result of the trial carried out is given herein below:

TABLE 1

Per cent Disease Index (PDI), Per cent disease Control (PDC) of Early Blight of Potato

| Treatment No. | Treatment Details | PDI | | | PDC | |
|---|---|---|---|---|---|---|
| | | Before First Spray | Before Second Spray | 15 Days After Third Spray | Before Second Spray | 15 days After Third Spray |
| T1 | Mancozeb 50.0% Chlorothalonil 25% WG (2:1 Ratio) | 8.47 | 23.57 | 37.65 | 23.29 | 33.22 |
| T2 | Mancozeb 56.3% Chlorothalonil 18.7% WG (3:1 Ratio) | 7.94 | 17.89 | 27.63 | 41.78 | 51.00 |
| T3 | Mancozeb 60.0% Chlorothalonil 15.0% WG (4:1 Ratio) | 7.48 | 11.91 | 17.43 | 61.23 | 69.08 |
| T4 | Mancozeb 62.5% Chlorothalonil 12.5% WG (5:1 Ratio) | 7.47 | 8.34 | 13.00 | 72.86 | 76.94 |
| T5 | Mancozeb 64.3% Chlorothalonil 10.7% WG (6:1 Ratio) | 7.76 | 11.14 | 16.41 | 63.75 | 70.89 |
| T6 | Mancozeb 65.6% Chlorothalonil 9.4% WG (7:1 Ratio) | 7.25 | 12.14 | 19.67 | 60.48 | 65.11 |
| T7 | Mancozeb 75% WP | 7.00 | 12.53 | 22.22 | 59.21 | 60.59 |
| T8 | Chlorothalonil 75% WP | 7.96 | 14.79 | 24.01 | 51.87 | 57.41 |
| T9 | Untreated Control | 7.23 | 30.73 | 56.38 | — | — |
| | S.E.± | 0.77 | 0.86 | 1.00 | — | — |
| | C.D. (at 5% level) | NS | 2.58 | 2.98 | — | — |

TABLE 2

Percent Disease Index (PDI), Percent Disease Control (PDC) of Late Blight of Potato:

| Treatment No. | Treatment Details | Percent Disease Index (PDI) & Percent Disease Control (PDC) | |
|---|---|---|---|
| | | PDI 15 Days After Third | PDC |
| T1 | Mancozeb 50.0% + Chlorothalonil 25% WG (2:1 Ratio) | 16.89 | 33.80 |
| T2 | Mancozeb 56.3% + Chlorothalonil 18.7% WG (3:1 Ratio) | 14.59 | 42.83 |
| T3 | Mancozeb 60.0% + Chlorothalonil 15.0% WG (4:1 Ratio) | 8.85 | 65.31 |
| T4 | Mancozeb 62.5% + Chlorothalonil 12.5% WG (5:1 Ratio) | 6.27 | 75.44 |
| T5 | Mancozeb 64.3% + Chlorothalonil 10.7% WG (6:1 Ratio) | 8.89 | 65.17 |
| T6 | Mancozeb 65.6% + Chlorothalonil 9.4% WG (7:1 Ratio) | 9.52 | 62.67 |
| T7 | Mancozeb 75% WP | 12.18 | 52.25 |
| T8 | Chlorothalonil 75% WP | 13.25 | 48.07 |
| T9 | Untreated Control | 25.51 | — |
| | S.E.± | 0.55 | — |
| | C.D. (at 5% level) | 1.64 | — |

TABLE 3

Yield of Potato Tuber (Quintal/Acre)

| Treatment No. | Treatment Details | Av. Yield (Quintal/Acre) |
|---|---|---|
| T1 | Mancozeb 50.0% + Chlorothalonil 25% WG (2:1 Ratio) | 35.60 |
| T2 | Mancozeb 56.3% + Chlorothalonil 18.7% WG (3:1 Ratio) | 37.77 |
| T3 | Mancozeb 60.0% + Chlorothalonil 15.0% WG (4:1 Ratio) | 43.13 |
| T4 | Mancozeb 62.5% + Chlorothalonil 12.5% WG (5:1 Ratio) | 47.93 |
| T5 | Mancozeb 64.3% + Chlorothalonil 10.7% WG (6:1 Ratio) | 44.97 |
| T6 | Mancozeb 65.6% + Chlorothalonil 9.4% WG (7:1 Ratio) | 41.97 |
| T7 | Mancozeb 75% WP | 39.70 |
| T8 | Chlorothalonil 75% WP | 39.57 |
| T9 | Untreated Control | 31.47 |
| | S.E.± | 0.91 |
| | C.D. (at 5% level) | 2.72 |

CONCLUSION

1. It was thus surprisingly found that the percent control of Early Blight of Potato by mancozeb+chlorothalonil at 5:1 at 76.94% was significantly superior over other ratios i.e. 2:1, 3:1, 4:1, 6:1 and 7:1.
2. Mancozeb+Chlorothalonil in the ratio of 5:1 also showed increased control of Early Blight of Potato than the single application of Mancozeb 75 WP and Chlorothalonil 75 WP i.e. 60.59% and 57.41%
3. The percent disease index recorded during the observation in untreated control treatment was 25.51%. Among all the treatments, the treatment of Mancozeb+Chlorothalonil at ratio 5:1 found to be statistically significant over all the ratios of Mancozeb+Chlorothalonil and with Mancozeb 75 WP and Chlorothabnil 75 WP in the control of Late Blight of Potato.
4. Highest tuber yield of potato recorded in treatment of Mancozeb+Chlorothalonil at ratio 5:1 i.e. 47.93 quintal/acre which was statistically significant over all other treatments.
5. It was thus concluded that the Mancozeb+Chlorothalonil at 5:1 was the best combination ratio over all other tested ratios of Mancozeb+Chlorothalonil to control both early and late blight disease of potato and to obtain highest tuber yield of potato.

Advantages of One or More Embodiments of the Present Invention

1. The present invention provides a combination of mancozeb and chlorothalonil at a synergistic ratio.

2. The compositions according to the present invention possess an improved dispersibility and suspensibility.
3. The compositions of the present invention display an improved and extended fungal control, reduced fungicide application rates and costs, less stringent use restrictions, improved selectivity, improved spectrum of fungi controlled, reduced costs, and reduced residue problems.
4. The water dispersible granular composition of mancozeb and chlorothalonil according to the invention possess superior attrition resistance without compromising on rapid dispersibility of the formulation and exhibits good suspensivity in water on being dispersed.

The invention claimed is:

1. A composition comprising a fungicidally effective amount of mancozeb and a fungicidally effective amount of chlorothalonil in a ratio of 5:1.
2. The composition as claimed in claim 1, wherein mancozeb is present from 55% to 65% by weight of the composition.
3. The composition as claimed in claim 1, wherein chlorothalonil is present from 10% to 15% by weight of the composition.
4. The composition as claimed in claim 1, wherein said composition comprises 62.5% by weight of mancozeb and 12.5% by weight of chlorothalonil.
5. The composition as claimed in claim 1, formulated as dust, powder, granules, pellets, tablets, dry flowable, wettable powder or water dispersible granules.
6. The composition as claimed in claim 1 wherein the total weight of mancozeb and chlorothalonil together is 75% by weight of the composition.
7. The composition as claimed in claim 5, wherein the composition is formulated as water dispersible granules.
8. The composition as claimed in claim 1 additionally comprising at least one agriculturally acceptable adjuvant selected from at least one dispersing agent; at least one wetting agent, at least one antifoam, at least one pH modifier, at least one surfactant and combinations thereof.
9. The composition as claimed in claim 8, wherein the dispersing agent is selected from salts of polystyrenesulphonic acids, salts of polyvinylsulphonic acids, salts of naphthalenesulphonic acid/formaldehyde condensates, salts of condensates of naphthalenesulphonic acid, phenolsulphonic acid and formaldehyde, and salts of lignosulphonic acid, polyethylene oxide/polypropylene oxide block copolymers, polyethylene glycol ethers of linear alcohols, reaction products of fatty acids with ethylene oxide and/or propylene oxide, furthermore polyvinyl alcohol, polyvinylpyrrolidone, copolymers of polyvinyl alcohol and polyvinylpyrrolidone and copolymers of (meth)acrylic acid and (meth)acrylic esters, furthermore alkyl ethoxylates and alkylarylethoxylates.
10. The composition as claimed in claim 8, wherein the wetting agent is selected from soaps; salts of aliphatic monoesters of sulphuric acid including but not limited to sodium lauryl sulphate; sulfoalkylamides and salts thereof including but not limited to N-methyl-N-oleoyltaurate Na salt; alkylarylsulfonates including but not limited to alkylbenzenesulfonates; alkylnaphthalenesulfonates and salts thereof and salts of ligninsulfonic acid.
11. The composition as claimed in claim 9, wherein the wetting agent is alkali metal salt of alkylnaphthalenesulfonate or an alkali metal salt of ligninsulfonic acid or a combination thereof.
12. The composition as claimed in claim 8, wherein the antifoaming agent is selected from silicone oil and magnesium stearate or a suitable combination thereof.
13. The composition as claimed in claim 8, wherein the pH modifier is selected from potassium carbonate, potassium hydroxide, sodium hydroxide and sodium dihydrogen phosphate.
14. The composition as claimed in claim 8, wherein the surfactant is selected from salts of polystyrenesulphonic acids; salts of polyvinylsulphonic acids; salts of naphthalenesulphonic acid/formaldehyde condensates; salts of condensates of naphthalenesulphonic acid, phenolsulphonic acid and formaldehyde; salts of lignosulphonic acid; polyethylene oxide/polypropylene oxide block copolymers; polyethylene glycol ethers of linear alcohols; reaction products of fatty acids with ethylene oxide and/or propylene oxide; polyvinyl alcohol; polyvinylpyrrolidone; copolymers of polyvinyl alcohol and polyvinylpyrrolidone; copolymers of (meth)acrylic acid and (meth)acrylic esters; and alkyl ethoxylates and alkylarylethoxylates.
15. A process for preparation of granular formulation comprising Mancozeb and Chlorothalonil, said process comprising:
   a. blending a fungicidally effective amount of mancozeb with a fungicidally effective amount of chlorothalonil in a ratio of 5:1 optionally with at least one adjuvant selected from at least one wetting agent, at least one dispersing agent, at least one antifoam, at least one stabilizing agent, at least one pH modifier, at least one surfactant or combinations thereof and water, to prepare slurry with total solid content of 50-58%;
   b. homogenizing said slurry by wet milling and sieving to remove course particles having diameter greater than 1000 microns;
   c. spray drying the slurry of step (b) through nozzle to obtain the granules of 100-500 micron;
   d. drying the granules of step (c) in a fluid bed dryer; and
   e. packing the dried granules.
16. The process as claimed in claim 15, wherein spray-drying of step (c) is carried out at the inlet temperature of 220 to 260° C. and outlet temperature of 95 to 115° C.

* * * * *